(12) United States Patent
Shibata et al.

(10) Patent No.: US 9,500,577 B2
(45) Date of Patent: Nov. 22, 2016

(54) SAMPLE ANALYZER

(75) Inventors: Masaharu Shibata, Kobe (JP); Toru Mizuhashi, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 403 days.

(21) Appl. No.: 13/593,168

(22) Filed: Aug. 23, 2012

(65) Prior Publication Data

US 2013/0047711 A1 Feb. 28, 2013

(30) Foreign Application Priority Data

Aug. 26, 2011 (JP) ................................ 2011-184939

(51) Int. Cl.
*G01N 1/00* (2006.01)
*G01N 15/14* (2006.01)
*G01N 35/00* (2006.01)
*G01N 35/10* (2006.01)

(52) U.S. Cl.
CPC ........ *G01N 15/14* (2013.01); *G01N 35/00732* (2013.01); *G01N 35/1004* (2013.01)

(58) Field of Classification Search
CPC .......... G01N 1/00; G01N 1/28; G01N 1/286; G01N 1/38
USPC ........................................................ 73/863
See application file for complete search history.

(56) References Cited

U.S. PATENT DOCUMENTS

| | | | |
|---|---|---|---|
| 6,902,703 B2* | 6/2005 | Marquiss et al. | 422/505 |
| 2007/0125442 A1* | 6/2007 | Tribble et al. | 141/27 |
| 2010/0108101 A1 | 5/2010 | Shibata et al. | |
| 2010/0114501 A1* | 5/2010 | Kondou et al. | 702/22 |
| 2012/0115213 A1* | 5/2012 | Hofstadler et al. | 435/287.2 |

FOREIGN PATENT DOCUMENTS

| | | |
|---|---|---|
| JP | 2003-254980 | 9/2003 |
| JP | 2008-046033 A | 2/2008 |

* cited by examiner

*Primary Examiner* — John Fitzgerald
*Assistant Examiner* — Rodney T Frank
(74) *Attorney, Agent, or Firm* — Brinks Gilson & Lione

(57) ABSTRACT

A sample analyzer for aspirating and analyzing a sample in a sample tube is disclosed. The sample analyzer comprises: a fluid processing section for aspirating liquid contained in a tube with a pipette and flowing the liquid through a fluid circuit; an obtaining section for obtaining identification information for identifying type of tube to be aspirated from; and a control unit. When identifying that the tube to be aspirated from is a cleaning liquid tube, the control unit controls the fluid processing section to aspirate substantially all the cleaning liquid in the cleaning liquid tube with the pipette and use all or partial amount of the aspirated cleaning liquid to clean the fluid circuit.

20 Claims, 9 Drawing Sheets

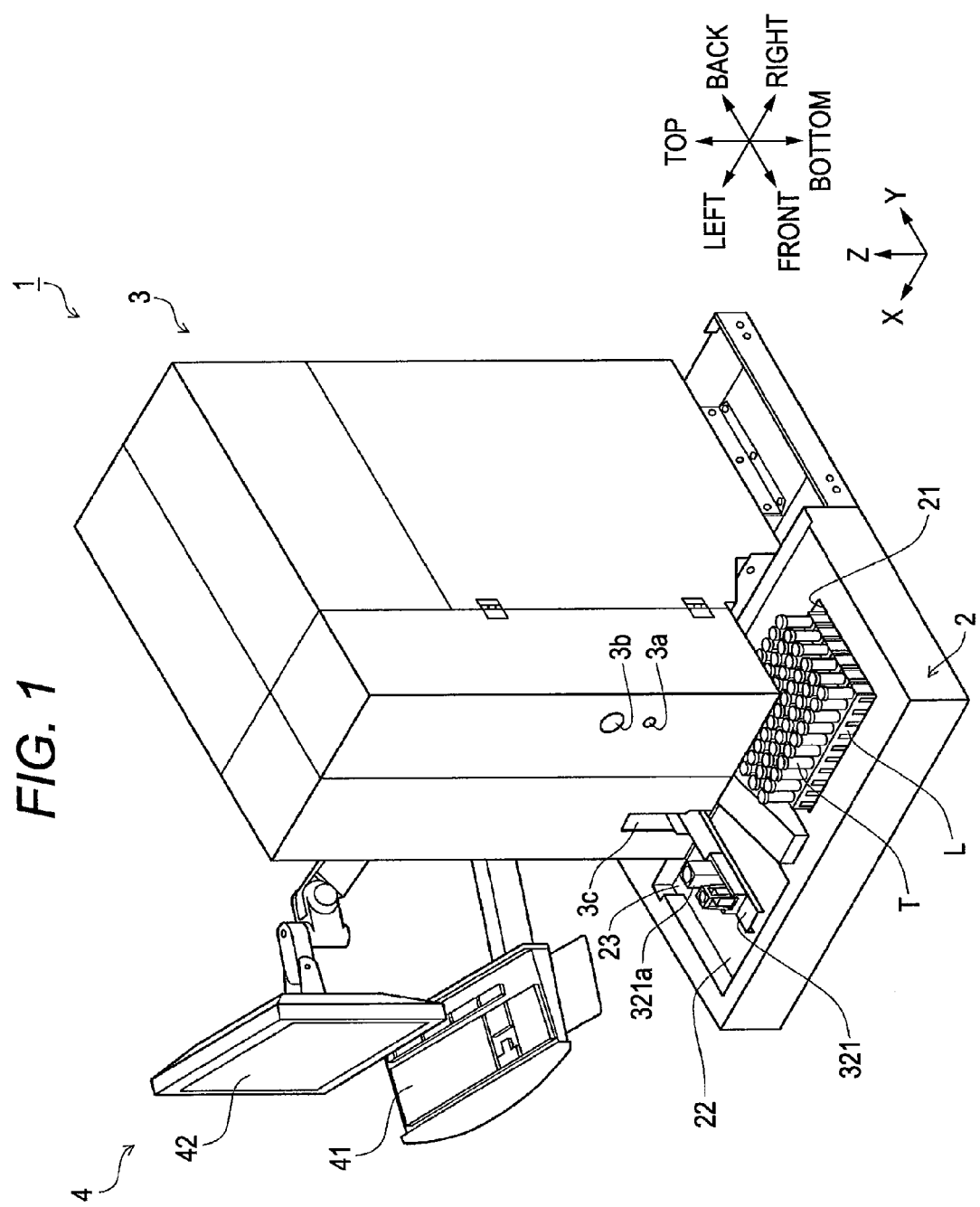

FIG. 3
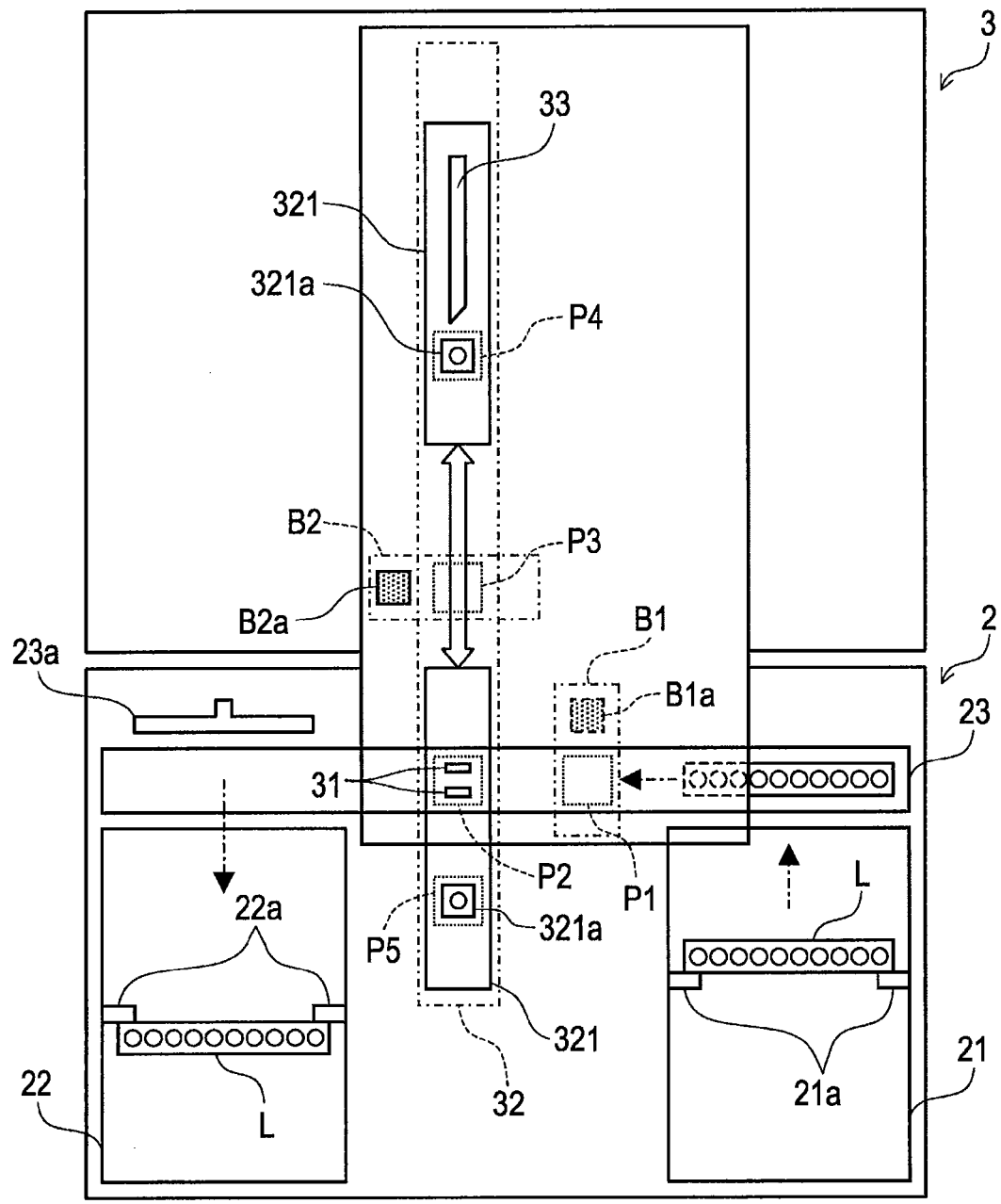
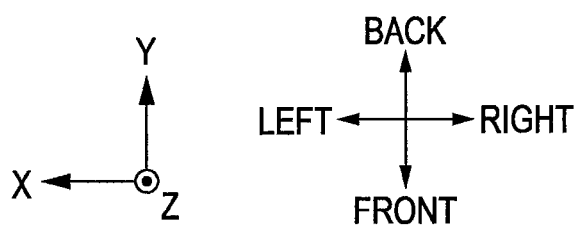

SAMPLE ANALYZER

RELATED APPLICATIONS

This application claims priority under 35 U.S.C. §119 to Japanese Patent Application No. 2011-184939 filed on Aug. 26, 2011, the entire content of which is hereby incorporated by reference.

BACKGROUND OF THE INVENTION

1. Field of the Invention

The present invention relates to a sample analyzer for processing samples such as blood.

2. Description of the Related Art

A sample analyzer for aspirating a sample from a sample tube, which contains a sample such as blood or urine, through a pipette, and analyzing the sample is known.

If the sample analyzer is used for a long period of time, dirt may accumulate in the fluid system such as the pipette, a flow path, a valve, a reaction tube. This may cause lowering accuracy and triggers an operation failure. Thus, the fluid system needs to be cleaned periodically or for every predetermined number of processing samples. Such a cleaning of the fluid system in Japanese Laid-Open Patent Application No. 2003-254980 discloses a specimen analyzer for aspirating cleaning liquid contained in a liquid tube through the pipette to clean a fluid circuit inside.

Since the amount of cleaning liquid necessary for one cleaning is constant, to carry out the automatic cleaning, the liquid tube is filled with an amount of cleaning liquid same or greater than the necessary amount and is supplied to the specimen analyzer. The specimen analyzer described in JP2003-254980 is configured to aspirate from a cleaning liquid tube only the cleaning liquid of the amount necessary for one cleaning and use it to clean the fluid circuit. The redundant amount of cleaning liquid is discarded together with the cleaning tube or only the redundant cleaning liquid is discarded for reuse of the cleaning liquid tube. However, these operations may cause the cleaning liquid to spill out and attach to the clothes and hands of the operator. Or the smell of the redundant cleaning liquid may spread to the surrounding by volatilization.

SUMMARY OF THE INVENTION

A first aspect of the present invention is a sample analyzer for aspirating and analyzing a sample in a sample tube, the sample analyzer comprising: an obtaining section for obtaining identification information for identifying type of a tube; a fluid processing section for aspirating liquid contained in a tube with a pipette and flowing the liquid through a fluid circuit; and a control unit; wherein when identifying based on the identification information obtained by the obtaining section that the tube supplied to the sample analyzer is a cleaning liquid tube containing cleaning liquid, the control unit controls the fluid processing section to aspirate substantially all amount of the cleaning liquid in the cleaning liquid tube with the pipette and use all or partial amount of the aspirated cleaning liquid to clean the fluid circuit.

A second aspect of the present invention is a sample analyzer for aspirating and analyzing a sample in a sample tube, the sample analyzer comprising: an obtaining section for obtaining identification information for identifying type of a tube; a fluid processing section for aspirating liquid contained in a tube with a pipette and flowing the liquid through a fluid circuit; and a control unit; wherein when identifying based on the identification information obtained by the obtaining section that the tube supplied to the sample analyzer is a cleaning liquid tube containing cleaning liquid, the control unit controls the fluid processing section to aspirate a predetermined amount of cleaning liquid for cleaning the fluid circuit from the cleaning liquid tube and then aspirate remaining cleaning liquid in the cleaning liquid tube.

A third aspect of the present invention is a sample analyzer for aspirating and analyzing a sample in a sample tube, the sample analyzer comprising: an obtaining section for obtaining identification information for identifying type of a tube; a fluid processing section for aspirating liquid contained in a tube with a pipette and flowing the liquid through a fluid circuit; and a control unit; wherein when identifying based on the identification information obtained by the obtaining section that the tube supplied to the sample analyzer is a cleaning liquid tube containing cleaning liquid, the control unit controls the fluid processing section to bring the pipette into contact with the inner bottom of the cleaning liquid tube and aspirate the cleaning liquid while having the pipette contacting the bottom, thus cleaning the fluid circuit using all or partial amount of the aspirated cleaning liquid.

BRIEF DESCRIPTION OF THE DRAWINGS

FIG. 1 is a perspective view showing an outer appearance of a sample analyzer according to an embodiment;

FIG. 3 is a plane view showing a configuration of a transportation unit and a measurement unit according to the embodiment;

DETAILED DESCRIPTION OF THE PREFERRED EMBODIMENTS

Figure 2C:
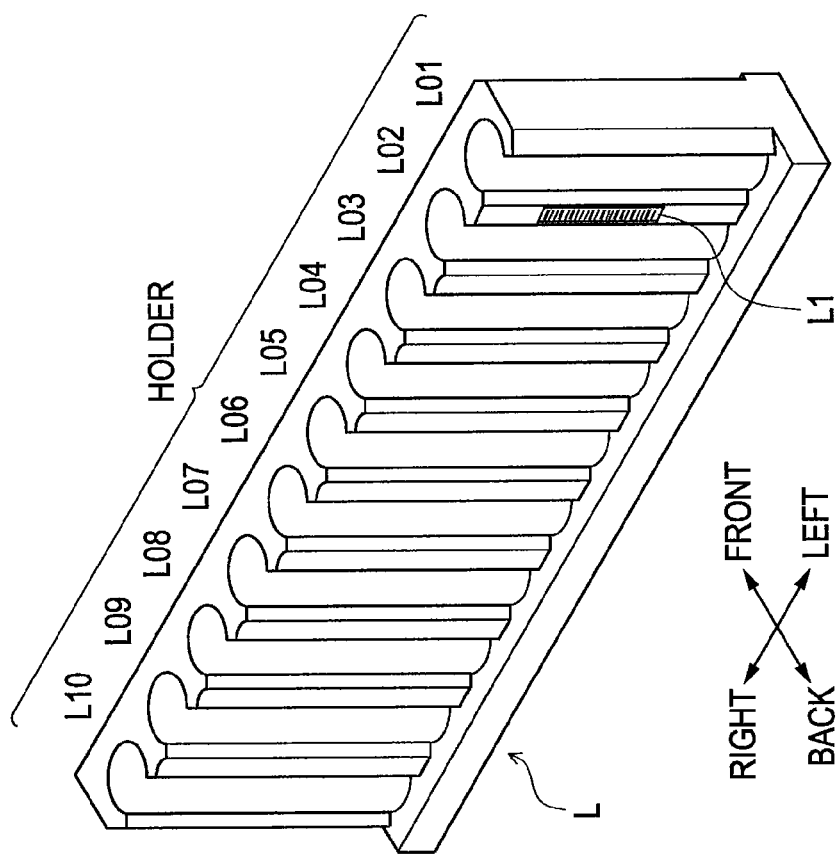
FIGS. 2A to 2C are views showing a configuration of a sample tube, a cleaning liquid tube, and a sample rack, respectively, according to the embodiment.

In the present embodiment, the present invention is applied to a sample analyzer for carrying out tests and analysis of blood.

A sample analyzer according to the present embodiment will be hereinafter described with reference to the drawings.

FIG. 1 is a perspective view showing an outer appearance of a sample analyzer 1. The sample analyzer 1 according to the present embodiment is configured by a transportation unit 2, a measurement unit 3, and an information processing unit 4.

The transportation unit 2 is arranged on a front side of the measurement unit 3, and includes a right table 21, a left table 22, and a rack transporting portion 23 connecting the right table 21 and the left table 22. The right table 21 and the left table 22 can accommodate a sample rack L formed with ten holders. The sample rack L can hold a sample tube T containing a sample, and a cleaning liquid tube W containing a cleaning liquid by the holders.

Figure 2A:
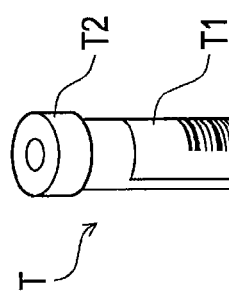
Figure 2B:
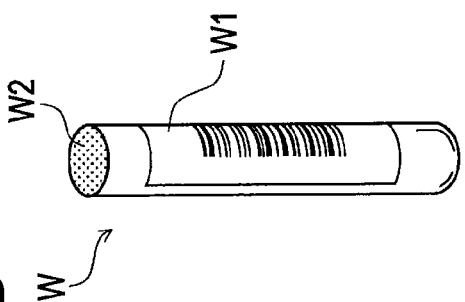

FIGS. 2A to 2C are views respectively showing the configuration of the sample tube T, the cleaning liquid tube W, and the sample rack L.

With reference to FIG. 2A, the sample tube T is a tubular container made of glass or synthetic resin having translucency, and has an upper end opened. A barcode label T1 is attached to a side surface of the sample tube T. A barcode including a sample ID for identifying the individual sample is printed on the barcode label T1. The sample tube T contains a whole blood sample taken from a patient, where the opening at the upper end is sealed by a lid T2. The lid T2 is made of rubber such that a piercer 33, to be described later, can be passed through.

With reference to FIG. 2B, the cleaning liquid tube W is a tubular container having the same size as the sample tube T, where the upper end is opened. A barcode label W1 is attached to a side surface of the cleaning liquid tube W. A barcode including a predetermined cleaning liquid ID for indicating that the cleaning liquid is contained therein is printed on the barcode label W1. The cleaning liquid tube W contains 4 mL of the cleaning liquid (e.g., chlorinated cleaning liquid) for cleaning the fluid circuit in the measurement unit 3, where the opening at the upper end is sealed by a lid W2 made of a film member. The fluid circuit of the measurement unit 3 will be described later with reference to FIG. 5.

With reference to FIG. 2C, the sample rack L is formed with holders L01 to L10 capable of perpendicularly holding the sample tube T and the cleaning liquid tube W. A barcode label L1 is attached to a side surface on the back side of the sample rack L. A barcode including a rack ID is printed on the barcode label L1.

Returning back to FIG. 1, the transportation unit 2 accommodates the sample rack L placed on the right table 21 by the user. The transportation unit 2 transports the sample rack L accommodated in the right table 21, and positions the sample rack L at a predetermined position of the rack transporting portion 23 so that the sample tube T or the cleaning liquid tube W is supplied to the measurement unit 3. Furthermore, the transportation unit 2 transports the sample rack L on the rack transporting portion 23 to the left table 22.

The measurement unit 3 includes an open/close button 3a, a start button 3b, a gripping portion 31 (see FIG. 3) for gripping the sample tube T and the cleaning liquid tube W, and a base 321. The base 321 is installed with a tube setting portion 321a for setting the sample tube T and the cleaning liquid tube W.

The measurement unit 3 brings out the sample tube T from the sample rack L by the gripping portion 31 (see FIG. 3) and transports the sample tube T to the inside of the measurement unit 3 when the sample tube T is positioned at a predetermined position of the rack transporting portion 23. The measurement unit 3 measures the sample contained in the sample tube T in the measurement unit 3. After the measurement is finished, the measurement unit 3 returns the sample tube T to the holder of the sample rack L where the tube was originally held.

The measurement unit 3 also brings out the cleaning liquid tube W from the sample rack L by the gripping portion 31 (see FIG. 3) and transports the cleaning liquid tube W to the inside of the measurement unit 3 even when the cleaning liquid tube W is positioned at a predetermined position of the rack transporting portion 23. The measurement unit 3 carries out a cleaning of the fluid circuit in the measurement unit 3 by use of the cleaning liquid contained in the cleaning liquid tube W. After the cleaning is finished, the measurement unit 3 returns the cleaning liquid tube W to the holder of the sample rack L where the tube was originally held. The fluid circuit of the measurement unit 3 will be described later with reference to FIG. 5. The cleaning of the fluid circuit will be described later with reference to FIGS. 8 and 9.

When the open/close button 3a is pushed by the user, the base 321 projects out to the front side of the measurement unit 3 through an opening 3c formed at the front surface of the measurement unit 3. The user can cut into measurements of the sample tube T being transported by the transportation unit 2 to preferentially carry out the measurement of the sample to perform the measurement urgently by setting the sample tube T in the sample tube setting portion 321a and pushing the start button 3b. Similarly, when an instruction of a prior measurement is input to the information processing unit 4 by the user, the base 321 projects out to the front side of the measurement unit 3.

When a cleaning instruction is input through the information processing unit 4 by the user as well, the base 321 similarly projects out to the front side of the measurement unit 3. The user can let the measurement unit 3 carry out a cleaning of the fluid circuit by use of the cleaning liquid in the cleaning liquid tube W by setting the cleaning liquid tube W onto the sample tube setting portion 321a and pushing the start button 3b.

The information processing unit 4 includes an input section 41 and a display section 42. The information processing unit 4 is communicably connected to the transportation unit 2, the measurement unit 3, and a host computer (see FIG. 7) through a communication network. The information processing unit 4 controls the operations of the transportation unit 2 and the measurement unit 3, performs analysis based on the measurement result carried out in the measurement unit 3, and transmits an analysis result to the host computer.

FIG. 3 is a plan view showing a configuration of the transportation unit 2 and the measurement unit 3. Although the illustration is omitted, various types of sensors for detecting the sample rack L, the sample tube T, and the cleaning liquid tube W are arranged at predetermined positions of the right table 21, the left table 22, and the rack transporting portion 23.

First, a case in which the sample in the sample tube T transported by the transportation unit 2 is measured will be described.

The sample rack L placed on the right table 21 is pushed at the front side surface by a rack feeding mechanism 21a, and thereby transported to the right end position of the rack transporting portion 23. The sample rack L positioned at the right end position of the rack transporting portion 23 is transported in a leftward direction by a belt (not shown) of the rack transporting portion 23.

A barcode unit B1 including a barcode reader B1a is provided near the middle of the rack transporting portion 23. When the holder of the sample rack L is positioned at a reading position P1 on the front side of the barcode reader B1a, a sensing mechanism (not shown) of the barcode unit B1 senses a presence or absence of the sample tube T at the holder. Such mechanism includes a mechanism capable of sandwiching the sample tube T from the front-back direction (Y axis direction). When the sample tube T is sandwiched, determination is made that the sample tube T is held at the holder positioned at the reading position P1.

If the sample tube T is held at the holder, the mechanism initiates to rotate the sandwiched tube and, and the sample ID is read from the barcode label T1 of the sample tube T by the barcode reader B1a while rotating the sample tube T. When the barcode label L1 of the sample rack L is positioned on the front side of the barcode reader B1a, the rack ID is read from the barcode label L1 of the sample rack L by the barcode reader B1a.

The sample tube T which sample ID is read by the barcode reader B1a is further transported in the leftward direction, and positioned at a retrieving position P2. The gripping portion 31 is provided at the retrieving position P2 in a manner of capable of being actuated in the up-down direction (Z axis direction). The sample tube T positioned at the retrieving position P2 is gripped by the gripping portion 31, and is brought out from the sample rack L in the upward direction (positive direction in Z axis). The transportation of the sample rack L is waited until the sample tube T is returned to the sample rack L.

The sample tube transporting portion 32 includes a base 321 where the sample tube setting portion 321a is installed, and a mechanism (not shown) for moving the base 321 forward and backward in a region surrounded with a chain dashed line.

When a sample tube T arrives at the retrieving position P2, the gripping portion 31 grips and brings up the sample tube T and stirs it. Subsequently, the base 321 is moved so that the sample tube setting portion 321a is positioned above the retrieving position P2. The gripping portion 31 is moved in a downward direction (negative direction in Z axis) in this state, so that the sample tube T gripped by the gripping portion 31 is set in the sample tube setting portion 321a.

The base 321 is then moved to the back side, and the sample tube setting portion 321a is positioned at a reading position P3 where the sample tube is faced to the barcode reader B2a of the barcode unit B2. Determination is then made by the holding determination mechanism (not shown) of the barcode unit B2 in this state on whether or not the sample tube T is set in the sample tube setting portion 321a. Such holding determination mechanism includes a mechanism capable of sandwiching the sample tube T from the left-right direction (X axis direction). When the sample tube T is sandwiched, determination is made that the sample tube T is held in the sample tube setting portion 321a positioned at the reading position P3. If the sample tube T is set in the sample tube setting portion 321a, the sample ID is read from the barcode label T1 of the sample tube T by the barcode reader B2a while rotating the sample tube T.

The base 321 is then moved to the back side, so that the sample tube setting portion 321a is positioned at an aspirating position P4 immediately below the piercer 33. Subsequently the piercer 33 is moved in the downward direction, and a predetermined amount of sample necessary for a measurement is aspirated from the sample tube T positioned at the aspirating position P4. The configuration of the piercer 33 will be described later with reference to FIGS. 4A and 4B.

After the aspiration of the sample by the piercer 33 is finished, the base 321 is moved to the front side, and the sample tube setting portion 321a is again positioned at the retrieving position P2. At the retrieving position P2, the sample tube T is taken out in the upward direction by the gripping portion 31. After the base 321 is moved to the back side in this state, the gripping portion 31 is moved in the downward direction (negative direction in Z axis), and the sample tube T is returned to the original holder of the sample rack L positioned in the rack transporting portion 23.

When the measurement of the samples of all the sample tubes T held in the sample rack L is finished in such manner, the sample rack L is fed to the left end position of the rack transporting portion 23. Subsequently, the sample rack L is pushed out to the left table 22 by a rack pushing mechanism 23a. The sample rack L positioned at the left table 22 is transported to the front side of the left table 22 by a rack feeding mechanism 22a.

As described above, even when the cleaning liquid tube W is held in the sample rack L, the cleaning liquid tube W is transported to the measurement unit 3 in a manner similar with the sample tube T. When having the cleaning liquid tube W held in the sample rack L, the cleaning liquid tube W and the sample tube T may be simultaneously held by one sample rack L.

After the cleaning liquid tube W is held by the sample rack L and transported by the transportation unit 2, the barcode label W1 of the cleaning liquid tube W is read by the barcode reader B1a. Thereafter, the cleaning liquid tube W is taken out by the gripping portion 31 at the retrieving position P2. Stirring is skipped for the cleaning liquid tube W. And the cleaning liquid ID is read from the barcode label W1 of the cleaning liquid tube W by the barcode reader B2a. The cleaning liquid tube W is then positioned at the aspirating position P4, and the cleaning liquid in the cleaning liquid tube W is aspirated by the piercer 33. The aspiration of the cleaning liquid by the piercer 33 will be described later with reference to FIGS. 4C and 4D. After the aspiration is finished, the cleaning liquid tube W is returned to the original holder of the sample rack L positioned in the rack transporting portion 23.

An operation to manually set a sample tube T on the sample tube setting portion 321a will now be described.

As described above, when the open/close button 3a (see FIG. 1) is pushed by the user, or when the instruction of the prior measurement is input through the information processing unit 4 by the user, the base 321 is moved towards the front side and the sample tube setting portion 321a is positioned at a setting position P5. The sample tube T is set in the tube setting portion 321a in this state.

When the measurement start button 3b (see FIG. 1) is pushed, the base 321 is moved to the back side so that the sample tube T is positioned at the reading position P3, and the sample ID is read from the barcode label T1 of the sample tube T by the barcode reader B2a while the sample tube T is rotating. The sample tube T is then positioned at the aspirating position P4, and the sample in the sample tube T is aspirated by the piercer 33. After the aspiration is finished, the sample tube setting portion 321a is again positioned at the setting position P5. The user takes out the sample tube T, from which aspiration is finished, from the sample tube setting portion 321a.

As described above, even when the cleaning instruction is input through the information processing unit 4 by the user, the base 321 is similarly projected out to the front side of the measurement unit 3 and the cleaning liquid tube W is transported into the measurement unit 3. After the cleaning liquid ID is read from the barcode label W1 of the cleaning liquid tube W by the barcode reader B2a, the cleaning liquid is aspirated by the piercer 33.

Figure 4:
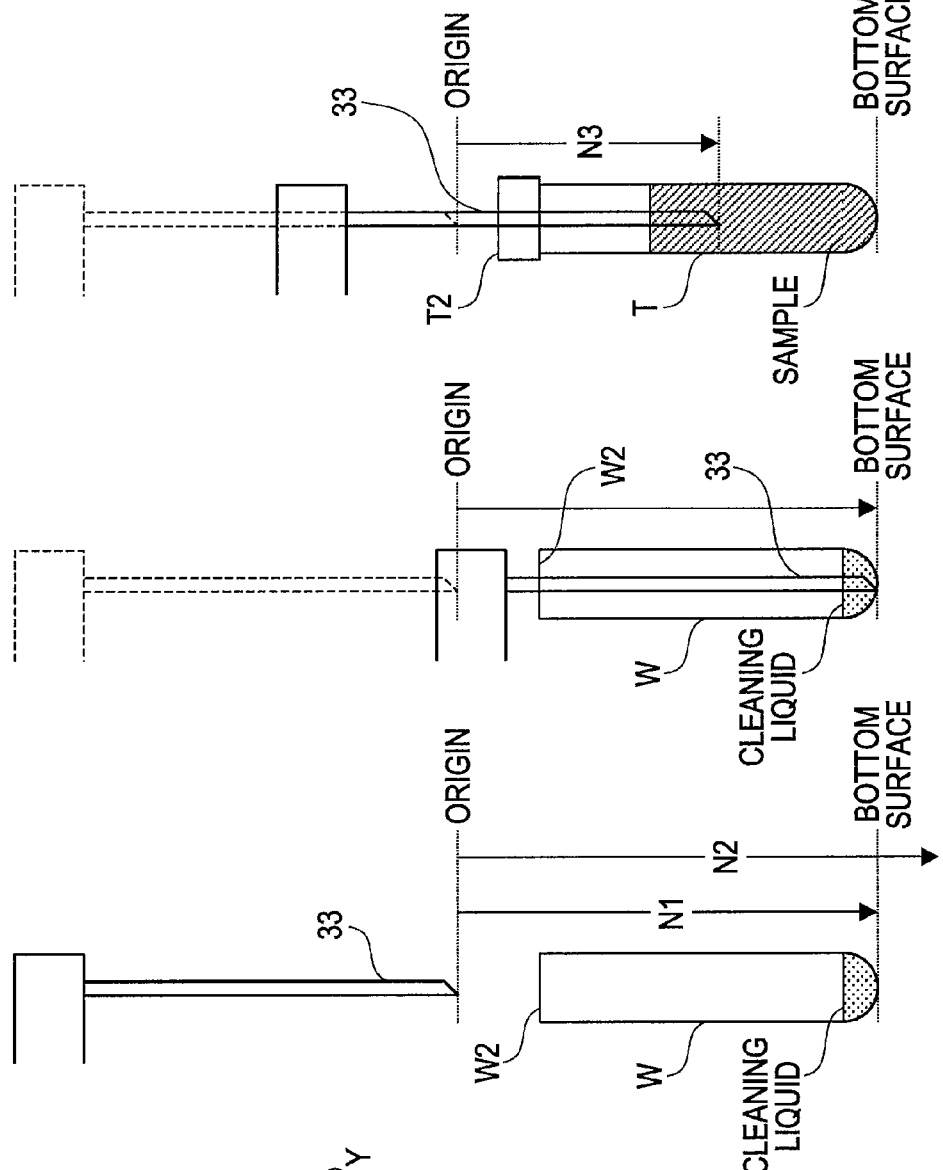
FIGS. 4A and 4B are enlarged views of a lower end of a piercer according to the embodiment.
FIGS. 4C to 4E are views describing the aspiration of the cleaning liquid and the sample by the piercer.

FIGS. 4A and 4B are respectively an enlarged view of lower end of the piercer 33 seen from the side surface, and an enlarged view of the piercer 33 seen from the lower side.

An aspiration path 33a is formed in the up-down direction inside the piercer 33. The aspiration path 33a is bent in the leftward direction near the lower end of the piercer 33, and is opened to outside through an opening 33b. The diameter of the piercer 33 is 1.5 mm, and the opening 33b is formed 1 mm above the lower end of the piercer 33. Two cutouts 33c symmetric with respect to a Y-Z plane are formed at the lower end of the piercer 33. The lower end of the piercer 33 has a pointed shape due to the two cutouts 33c.

Since the piercer 33 is configured in such manner, the lower end of the piercer 33 can penetrate through the lid W2 when the piercer 33 is lowered from the upper side of the cleaning liquid tube W. Furthermore, when the lower end of the piercer 33 makes contact with the bottom surface of the cleaning liquid tube W, the cleaning liquid can be aspirated through the aspiration path 33a to the bottom surface of the cleaning liquid tube W since the opening 33b is formed 1 mm above the lower end of the piercer 33.

FIGS. 4C and 4D are views describing the aspiration of the cleaning liquid by the piercer 33 from the cleaning liquid tube W positioned at the aspirating position P4.

With reference to FIG. 4C, the lower end of the piercer 33 is first positioned at an origin when aspirating the cleaning liquid from the cleaning liquid tube W. A pulse for actuating a stepping motor 306 (see FIG. 6) connected to a mechanism for moving the piercer 33 in the up-down direction is then input to the motor 306 at a predetermined time interval until the total number of input pulses reaches N2. The number of pulses N2 is a value greater than a number of pulses N1 that is necessary for actuating the piercer 33 to move the lower end of the piercer 33 from the origin to the bottom surface of the cleaning liquid tube W.

Thus, as shown in FIG. 4D, when the pulse is input at a predetermined time interval to the stepping motor 306, the lower end of the piercer 33 makes contact with the bottom surface of the cleaning liquid tube W before the total number of input pulses reaches N2. Thereafter, the pulse is continuously input to the stepping motor 306, but the stepping motor 306 will lose synchronism (step-out) since the lower end of the piercer 33 is contacting the bottom surface of the cleaning liquid tube W. Therefore, the lower end of the piercer 33 continues to be positioned at the bottom surface of the cleaning liquid tube W without damaging the bottom surface of the cleaning liquid tube W. Thereafter, the input of the pulse to the stepping motor 306 is terminated when the total number of input pulses reaches N2. The lower end of the piercer 33 is positioned at the bottom surface of the cleaning liquid tube W in such manner.

In contrast, aspiration of a sample by the piercer 33 from the sample tube T positioned at the aspirating position P4 is carried out in a following manner. In such case, a number of pulses N3 is input to the stepping motor 306, as shown in FIG. 4E.

Specifically, when aspirating the sample from the sample tube T, after the lower end of the piercer 33 is positioned at the origin, the pulse is input to the stepping motor 306 at a predetermined time interval until the total number of input pulses reaches N3. In this case, as opposed to the aspiration of the cleaning liquid, the piercer 33 is lowered to pass through the lid T2 of the sample tube T so that the stepping motor 306 does not lose synchronism even when resisting the lowering of the piercer 33. In the present embodiment, CPU 401 is capable of controlling the torque of the stepping motor 306 by adjusting a current applied to the motor 306.

Therefore, to pierce the lid T2 of the sample tube T without causing the synchronism lost, CPU 401 makes higher the torque of the motor 306 than that for piercing the lid W2 of the cleaning liquid W, by increasing the current applied to the stepping motor 306. Such control manner of the motor is disclosed in the U.S. Pat. No. 7,981,384 and that is herein corporate by reference.

The number of pulses N3 is a value smaller than the pulse N1. The number of pulses N3 is a preset value so that the lower end of the piercer 33 is positioned at least lower than the liquid level of the sample. The lower end of the piercer 33 is thus lowered to a predetermined position above the bottom surface at inside the sample tube T, and the sample is aspirated at such position.

Figure 5:
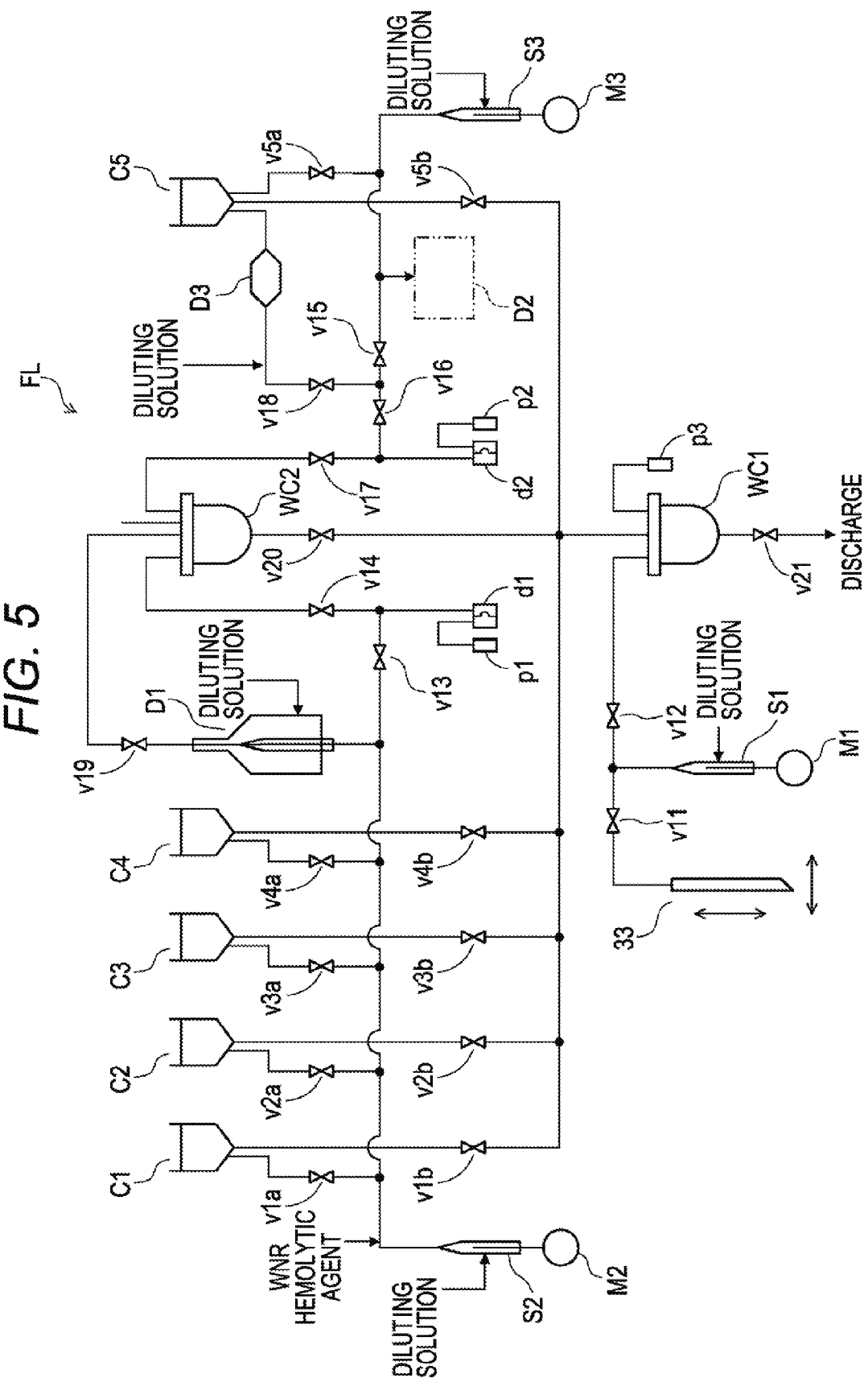
FIG. 5 is a view showing the main parts of a fluid processing section of the measurement unit according to the embodiment.

FIG. 5 is a view showing the main parts of the fluid processing section of the measurement unit 3.

As shown in FIG. 5, the fluid processing section FL includes, as a main configuration, the piercer 33, the stepping motor 306 (see FIG. 6) for moving the piercer 33 up and down, and the fluid circuit for flowing the liquid aspirated by the piercer 33.

The fluid circuit includes, as a main configuration, reaction chambers C1 to C5 for preparing a specimen, detectors D1 to D3 for detecting a component contained in the specimen prepared in the reaction chamber, a plurality of valves v1a to v5a, v1b to v5b, v11 to v21 for switching the flow path through which the liquid flows, syringe pumps S1 to S3 for applying pressure to flow the liquid to the flow path, diaphragm pumps d1, d2, and pressure adjusting units p1 to p3.

The reaction chamber C1 is a reaction chamber for preparing a specimen for performing analysis related to the number of abnormal cells/immature cells (WPC). The reaction chamber C2 is a reaction chamber for preparing a specimen for performing analysis related to the white blood cell category (WDF). The reaction chamber C3 is a reaction chamber for preparing a specimen for performing analysis related to the white blood cell/nucleated red blood cell (WNR). The reaction chamber C4 is a reaction chamber for preparing a specimen for performing analysis related to reticulocyte (RET) and blood platelet (fluorescent) (PLT-F). The reaction chamber C5 is a reaction chamber for preparing a specimen for performing analysis related to the red blood cells (RBC), the blood platelet (PLT), and the hemoglobin (HGB). The reaction chambers C1 to C5 are supplied with a predetermined amount of stain fluid, hemolytic agent, and diluted solution by a fluid circuit (not shown).

The detector D1 includes a flow cell and an optical detector for performing measurement by a flow cytometry using a semiconductor laser. The optical information (side fluorescent signal, forward scattered light signal, side scattered light signal) are detected as data of the sample from the white blood cells, the nucleated red blood cells and the like in the specimen. In the detector D1, the WPC measurement, the WDF measurement, the WNR measurement, the RET measurement, and the PLT-F measurement are carried out. The RBC/PLT measurement is carried out in the detector D2, and the HGB measurement is carried out in the detector D3.

The motors M1 to M3 respectively operate the syringe pumps S1 to S3. When the syringe pumps S1 to S3 are operated, positive pressure or negative pressure is applied on the distal end portion of each of the syringe pumps S1 to S3.

The valves v1a to v5a, v1b to v5b, and v11 to v21 can open and close the fluid circuit. The diaphragm pumps d1, d2 respectively aspirates the liquid by the pressure generated by the pressure adjusting units p1, p2 and supplies the aspirated liquid into the fluid circuit. Waste fluid chambers WC1, WC2 are chambers for storing waste fluid. The upper part of the waste fluid chamber WC1 is opened so that the interior of the waste fluid chamber WC1 becomes equal to the atmospheric pressure.

The fluid circuit is configured so that a predetermined amount of diluting solution can be supplied to the downstream of fluid lines that are connected to the syringe pumps S1 to S3, the detector D1, and the detector D3. A predetermined amount of WNR hemolytic agent can be supplied by a circuit to the downstream of fluid line that is connected to the syringe pump S2.

After the sample tube T is positioned at the aspirating position P4, the piercer 33 is inserted to the sample tube T and the sample is aspirated by the piercer 33. The piercer 33 moves into interior of the measurement unit 3, then the aspirated sample is dispensed into the any one of reaction chambers C1 to C5. In the reaction chambers C1 to C5, the specimen to be used in the measurement is prepared from the dispensed sample. The prepared specimen is brought to the detectors D1 to D3 through the fluid circuit shown in FIG. 5, and detection is performed in the detectors D1 to D3. After the detection is finished, the specimen in the detectors D1 to D3 is discharged to the waste fluid chamber WC2, and the specimen in the reaction chambers C1 to C5 is discharged to the waste fluid chamber WC1.

The pollution may accumulate in the fluid circuit shown in FIG. 5 if the measurement of the sample is repeatedly carried out in such manner and the sample analyzer 1 is used over a long period time, which may lower the detection accuracy and cause operation failure. Thus, the cleaning liquid needs to be flowed through the fluid circuit to periodically clean the fluid circuit.

When cleaning the fluid circuit using the cleaning liquid, the user causes the cleaning liquid tube W to be transported by the measurement unit 3 or the cleaning liquid tube W to be transported by the rack transporting portion 23. Thus, the cleaning liquid is aspirated from the cleaning liquid tube W positioned at the aspirating position P4, and the cleaning of the fluid circuit in the measurement unit 3 is carried out.

Figure 6:
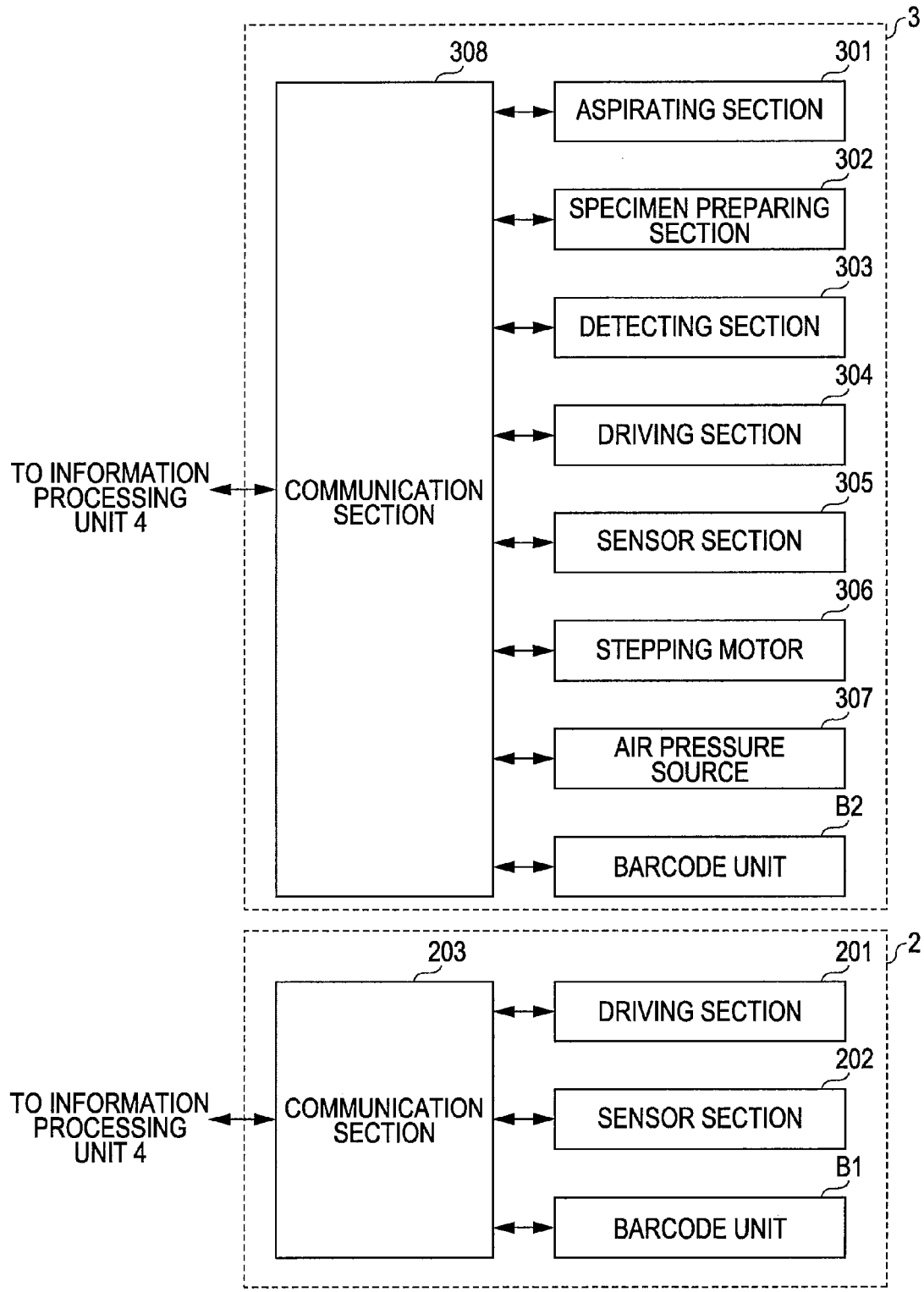
FIG. 6 is a view showing a configuration of the transportation unit and the measurement unit according to the embodiment.

FIG. 6 is a view showing a configuration of the transportation unit 2 and the measurement unit 3.

The transportation unit 2 includes a driving section 201, a sensor section 202, the barcode unit B1, and the communication section 203.

The driving section 201 includes a mechanism for transporting the sample rack L in the transportation unit 2, and the sensor section 202 includes a sensor for detecting the sample rack L at each position in the transportation unit 2. As described above, the barcode unit B1 includes the holding determination mechanism (not shown), and the barcode reader B1a.

The communication section 203 is communicably connected to the information processing unit 4. Each section of the transportation unit 2 is controlled by the information processing unit 4 through the communication section 203. The signal output from each section of the transportation unit 2 is transmitted to the information processing unit 4 through the communication section 203.

The measurement unit 3 includes an aspirating section 301, a specimen preparing section 302, a detecting section 303, a driving section 304, a sensor section 305, a stepping motor 306, an air pressure source 307, a barcode unit B2, and a communication section 308.

The aspirating section 301 includes a mechanism for aspirating the sample in the sample tube T and the cleaning liquid in the cleaning liquid tube W through the piercer 33.

The specimen preparing section 302 includes the reaction chambers C1 to C5, where the aspirated sample, the reagent, and the like are mixed and stirred in each reaction chamber to prepare the specimen for measurement. The detecting section 303 includes detectors D1 to D3, where the specimen prepared by the specimen preparing section 302 is measured.

The driving section 304 includes a mechanism for transporting the sample tube T and the cleaning liquid tube W in the measurement unit 3, a mechanism for driving the gripping portion 31, a mechanism for driving the sample tube transporting portion 32, a mechanism for moving the piercer 33 in the measurement unit 3, a mechanism for driving the motors M1 to M3, and a mechanism for opening and closing the valves v1a to v5a, v1b to v5b, v11 to v21. The sensor section 305 includes a sensor for detecting the pushing of the open/close button 3a and the measurement start button 3b, and the sensor for detecting the sample tube T and the cleaning liquid tube W at each position in the measurement unit 3. The barcode unit B2 includes the holding determination mechanism (not shown) and a barcode reader B2a, as described above.

The stepping motor 306 is connected to a mechanism for moving the piercer 33 up and down. When the cleaning liquid in the cleaning liquid tube W is aspirated by the piercer 33, a signal indicating a number of pulses N2 (see FIG. 4C) and a number of pulses to be input in one second (pulses/second) is input to the stepping motor 306 after the lower end of the piercer 33 is positioned at the origin. Such signal is input from the information processing unit 4 through the communication section 308. As shown in FIG. 4D, the lower end of the piercer 33 makes contact with the bottom surface of the cleaning liquid tube W. Similarly, when the sample in the sample tube T is aspirated by the piercer 33, a signal indicating a number of pulses N3 (see FIG. 4E) and a number of pulses to be input in one second is input to the stepping motor 306 after the lower end of the piercer 33 is positioned at the origin. The air pressure source 307 supplies pressure to the pressure adjusting units p1 to p3.

The communication section 308 is communicably connected to the information processing unit 4. Each section of the measurement unit 3 is controlled by the information processing unit 4 through the communication section 308. The signal output from each section of the measurement unit 3 is transmitted to the information processing unit 4 through the communication section 308.

Figure 7:
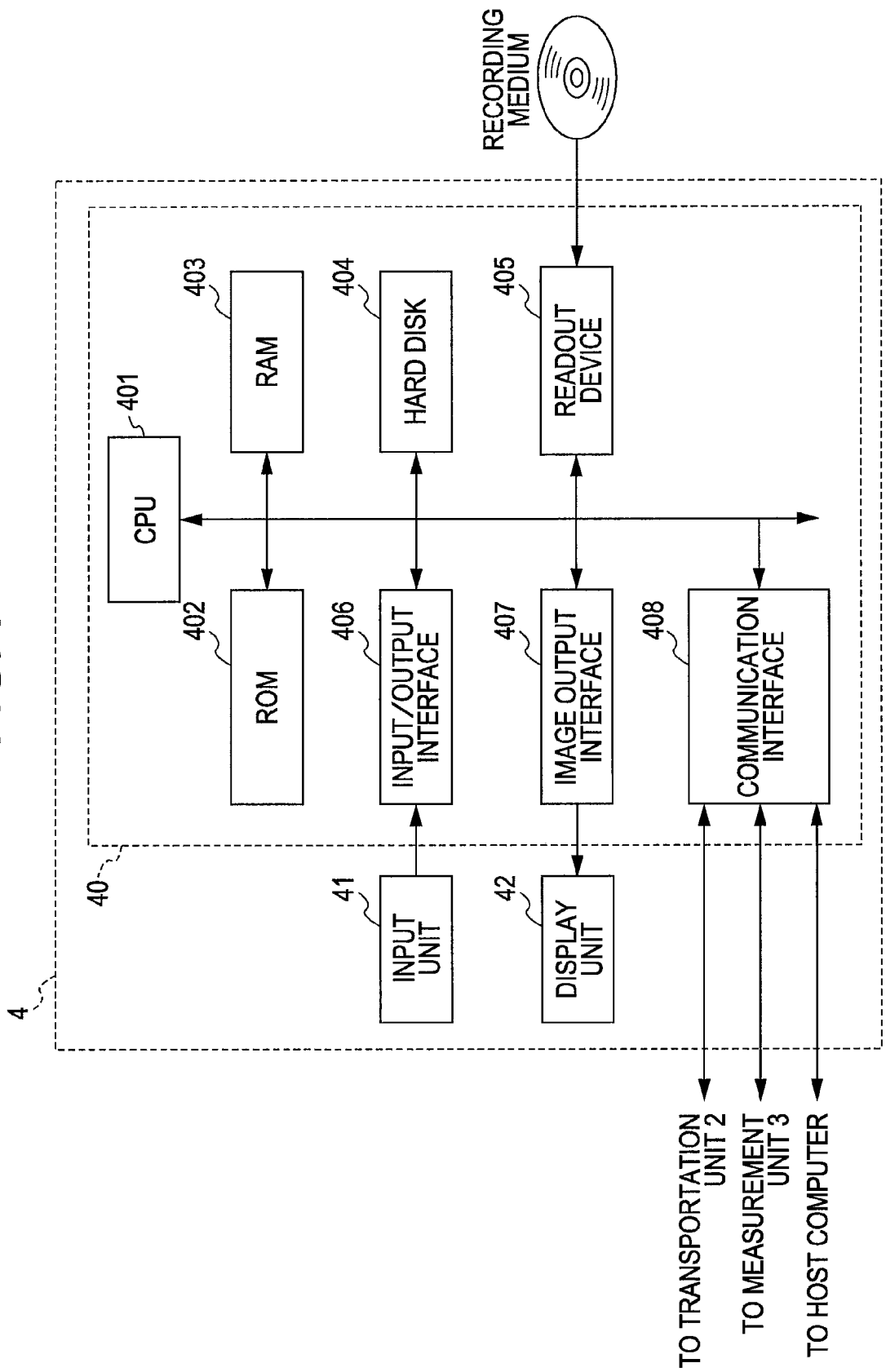
FIG. 7 is a view showing a configuration of an information processing unit according to the embodiment.

FIG. 7 is a view showing a configuration of the information processing unit 4.

The information processing unit 4 includes a personal computer, and is configured by a main body 40, an input unit 41, and a display unit 42. The main body 40 includes a CPU 401, a ROM 402, a RAM 403, a hard disk 404, a readout device 405, an input/output interface 406, an image output interface 407, and a communication interface 408.

The CPU 401 can execute computer programs stored in the ROM 402 and the computer programs loaded in the RAM 403. The RAM 403 is used to read out the computer programs recorded on the ROM 402 and the hard disk 404. In executing the computer program, the ROM 403 is used as a work region of the CPU 401.

The hard disk 404 is stored with various computer programs to be executed by the CPU 401 such as operating system and application program, as well as data used in executing the computer program. Specifically, in addition to the fixed cleaning liquid ID defined in advance indicating that the cleaning liquid is contained, the computer program and the data used for the measurement and the analysis, the computer program and the data for controlling each section of the measurement unit 3 and the transportation unit 2 are stored.

The readout device 405 is configured by a CD-ROM drive, DVD-ROM drive, or the like and is capable of reading out the computer program or data recorded in a recording medium. The input/output interface 406 is connected to the input unit 41 including a mouse and a keyboard, where the user uses the input unit 41 to input the instruction and data to the information processing unit 4. The image output interface 407 is connected to the display unit 42 configured by a display, or the like, and outputs a picture signal corresponding to the image data to the display unit 42. The display unit 42 displays an image based on the input picture signal. The data is transmitted and received with respect to the transportation unit 2, the measurement unit 3, and the host computer by the communication interface 408.

Figure 8:
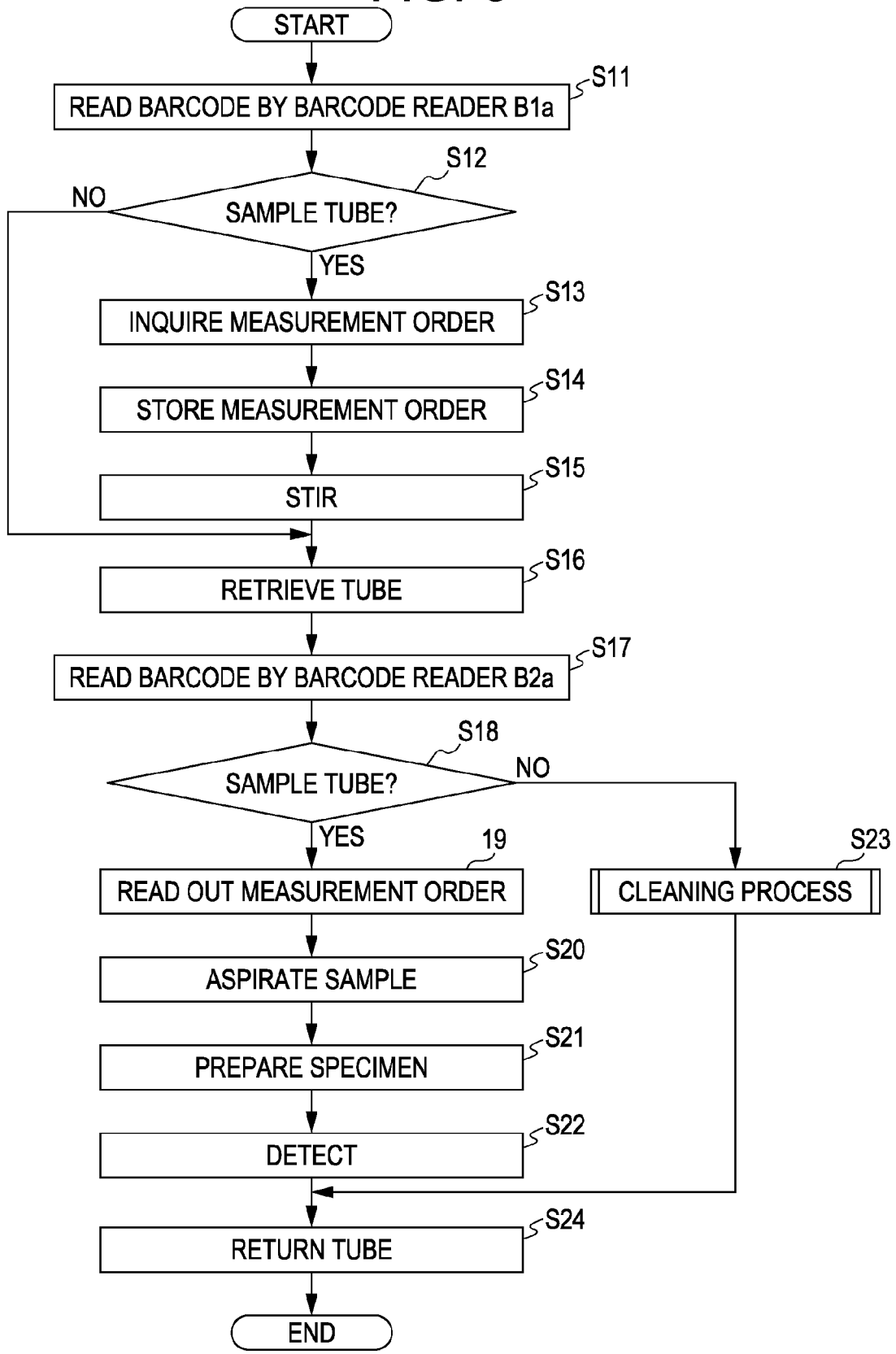
FIG. 8 is a flowchart showing a measuring process and a cleaning process carried out by the information processing unit according to the embodiment.

FIG. 8 is a flowchart showing a measuring process and a cleaning process carried out by the information processing unit 4. The processes of FIG. 8 are triggered by detecting that the sample tube T or the cleaning liquid tube W are held in the holder of the sample rack L positioned at the reading position P1.

The CPU 401 of the information processing unit 4 reads the barcode label of the tube positioned at the reading position P1 by the barcode reader B1a (S11) to determine whether the tube is the sample tube T (S12). Such determination is carried out based on whether or not the read content of the barcode reader B1 matches the cleaning liquid ID. In other words, determination is made that the tube is the cleaning liquid tube W if the read content matches the cleaning liquid ID, and determination is made that the tube is the sample tube T if the read content does not match the cleaning liquid ID.

When the tube is the sample tube T (S12: YES), the CPU 401 makes an inquiry of the measurement order to the host computer (see FIG. 7) based on the read content (sample ID) of S11 (S13). The measurement order related to each sample is stored in the host computer in advance. The CPU 401 stores the acquired measurement order in the hard disk 404 as a result of the inquiry (S14). The sample tube T is then transported to the retrieving position P2 by the transportation unit 2. The CPU 401 controls the gripping portion 31 to grip the sample tube T and to rotate it over plural times (moves the sample tube T so that the bottom of the sample tube T comes to a position higher than the head) to stir the sample tube T (S15), and then the CPU 401 causes the gripping portion 31 to draw the sample tube T into the measurement unit 3 (S16).

When the tube is the cleaning liquid tube W (S12: NO), the processes of S13 to S15 are skipped. The cleaning liquid tube W is then transported to the retrieving position P2 by the transportation unit 2. The CPU 401 controls the gripping portion 31 to grip the cleaning liquid tube W and to draw the cleaning liquid tube W into the measurement unit 3 (S16). The drawn sample tube T or the cleaning liquid tube W is set in the sample tube setting portion 321a, and positioned at the reading position P3.

The CPU 401 then commands the barcode reader B2a to read barcode label of the tube positioned at the reading position P3 (S17), and checks whether such tube is the sample tube T (S18). Such check is carried out similar to the step S12.

When the tube is the sample tube T (S18: YES), the CPU 401 identifies a measurement order that corresponds to the read content (sample ID) obtained in the step S17 among a plural of measurement orders that were stored in the hard disk 404 in the step S14 (S19). The CPU 401 causes the base 321 to move backward, to transport the sample tube T to the aspirating position P4, and performs the measurement of the sample. In other words, the CPU 401 controls the aspirating section 301 to aspirate the sample of the sample tube T (S20) as described in FIG. 4E, controls the specimen preparing section 302 to prepare the specimen in the reaction chambers C1 to C5 using the aspirated sample (S21), and performs the detection with the detectors D1 to D3 (S22). After the measurement is finished, the sample tube T is returned to the original holder of the sample rack L of the rack transporting portion 23 (S24).

When the tube positioned at the reading position P3 is the cleaning liquid tube W (S18: NO), such cleaning liquid tube W is transported to the aspirating position P4, and the cleaning process is carried out (S23). The cleaning process will be described later with reference to FIG. 9. After the cleaning process is finished, the cleaning liquid tube W is returned to the original holder of the sample rack L of the rack transporting portion 23 (S24).

If the base 321 is drawn to the front side of the measurement unit 3, and the sample tube T or the cleaning liquid tube W are set onto the tube setting portion 321a in a manual manner, steps S11 to S15 are omitted. In other words, if the sample tube T or the cleaning liquid tube W is manually set in the tube setting portion 321a, the sample tube T or the cleaning liquid tube W is drawn into the measurement unit 3 (S16), and positioned at the reading position P3. The sample ID or the cleaning liquid ID is then read by the barcode reader B2a (S17), and the processes the step of S18 and following steps are performed. In this case, if determined that the tube positioned at the reading position P3 is the sample tube T according to the read content of the barcode reader B2a (S18: YES), the inquiry of the measurement order and the storage of the measurement order are carried out based on the read content (sample ID), similar to S13 and S14.

Figure 9:
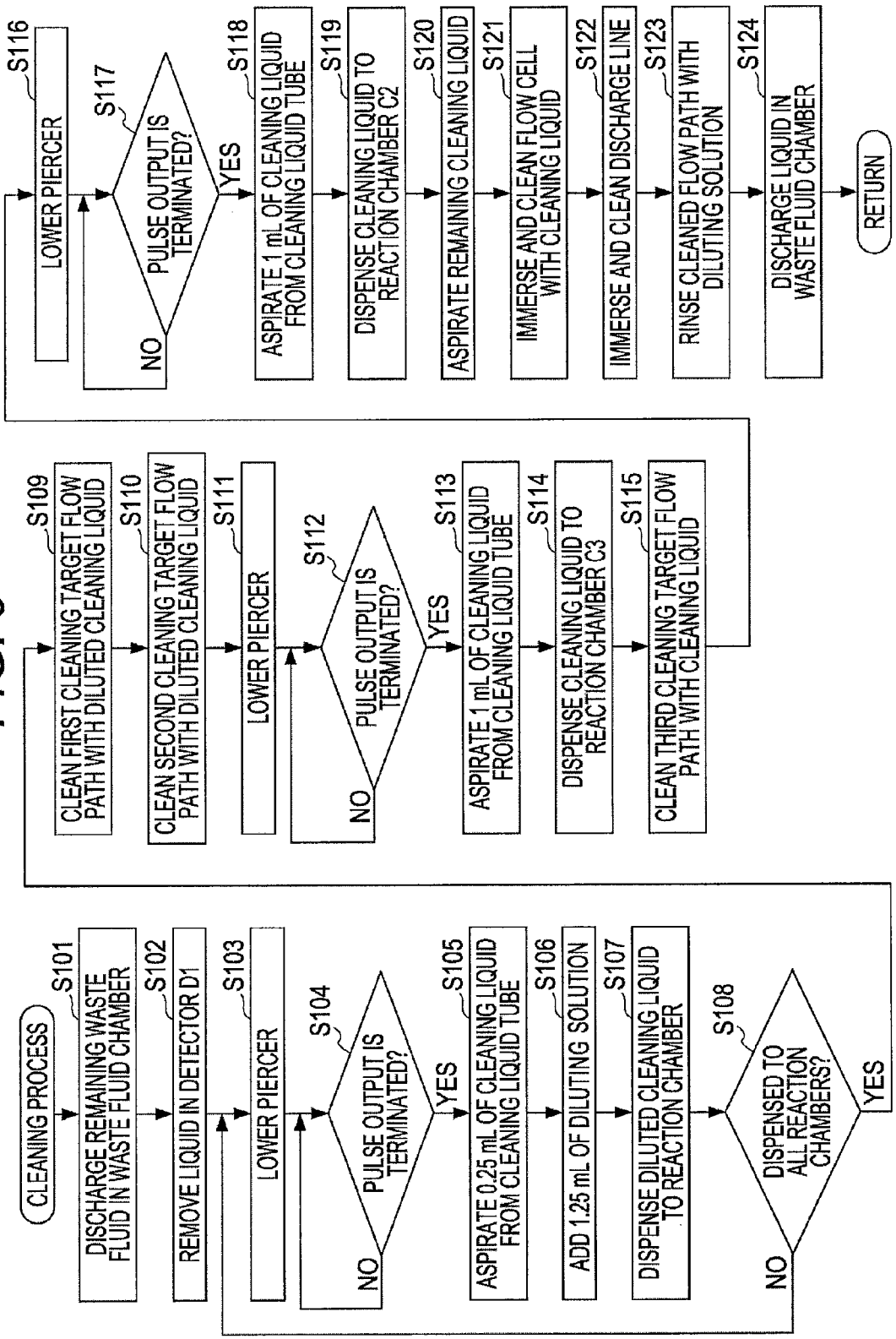
FIG. 9 is a flowchart showing the cleaning process carried out by the information processing unit according to the embodiment.

FIG. 9 is a flowchart showing the cleaning process carried out by the information processing unit 4. The cleaning process will be hereinafter described with reference to the fluid circuit shown in FIG. 5. Note that the valves in the fluid circuit are normally closed unless particularly stated otherwise.

The CPU 401 of the information processing unit 4 first causes the valve v21 to open and controls the pressure adjustment unit p3 to pressurize the waste fluid chamber WC1 to discharge the specimen remaining in the waste fluid chamber WC1. The valve v21 is then closed and the valve v20 is opened, and the waste fluid chamber WC1 is depressurized by the pressure adjustment unit p3 to feed the specimen remaining in the waste fluid chamber WC2 to the waste fluid chamber WC1. The valve v20 is then closed and the valve v21 is opened, and the waste fluid chamber WC1 is pressurized by the pressure adjustment unit p3 to discharge the specimen fed to the waste fluid chamber WC1 (S101).

The CPU 401 then carries out an operation of removing the liquid of the flow cell (S102). Specifically, the CPU 401 causes the valves v13 and v19 to open and causes the pressure adjustment unit p1 to depressurizes the diaphragm pump d1 to remove the liquid in the flow cell of the detector D1. The valves v13 and v19 are then closed and the valve v14 is opened, and the diaphragm pump d1 is pressurized by the pressure adjustment unit p1 to feed the liquid removed from the flow cell to the waste fluid chamber WC2. The removal of the liquid in S102 is completed before the process of S109 is started.

Then the lower end of the piercer 33 is positioned at the origin, as shown in FIG. 4C. The CPU 401 then makes the piercer 33 to lower by outputting a pulse to the stepping motor 306 at a predetermined time interval (S103). In this case, the CPU 401 continues to output the pulse until the total number of output pulse reaches N2 (S104: YES). The lower end of the piercer 33 thus makes contact with the bottom surface of the tube W, as shown in FIG. 4D.

The CPU 401 then operates the valve v11 to open and drives the motor M1 to operate the syringe pump S1, thus applying negative pressure to the piercer 33 and aspirating the cleaning liquid through the piercer 33. In the present embodiment, a volume to be aspirated by one actuation of the syringe pump S1 is 0.25 mL. Here, when the syringe pump S1 is actuated once, 0.25 mL of cleaning liquid is aspirated (S105). The aspirated cleaning liquid is accumulated in the inner path of the piercer 33. The CPU 401 then controls the piercer 33 to move in the measurement unit 3 to locate above the chamber C1. The CPU 401 drives the motor M1 to operate the syringe pump S1, thus applying positive pressure to the piercer 33 while supplying 1.25 mL of diluting solution into the piercer 33 (S106). Thereby, 1.5 mL of diluted cleaning liquid is dispensed to the reaction chamber C1 (S107).

The CPU 401 repeats the processes S103 to S107 until the diluted cleaning liquid is generated and dispensed to all the reaction chambers (S108). Thus, 1.5 mL of diluted cleaning liquid is dispensed to each of the reaction chambers C1 to C5.

The CPU 401 performs cleanings of flow path from the reaction chamber C1 to the waste fluid chamber WC2 through the valves v1a, v13, v14, the flow path from the reaction chamber C2 to the waste fluid chamber WC2 through the valves v2a, v13, v14, the flow path from the reaction chamber C3 to the waste fluid chamber WC2 through the valves v3a, v13, v14, and the flow path from the reaction chamber C4 to the waste fluid chamber WC2 through the valves v4a, v13, v14 (hereinafter these flow paths are collectively called the first cleaning target flow path) by use of the prepared diluted cleaning liquid (S109). In other words, the CPU 401 operates the valves v1a to v4a, v13, and v14 to move the diluted cleaning liquid in the reaction chambers C1 to C4 to the waste fluid chamber WC2 by the pressure adjustment unit p1 and the diaphragm pump d1. The CPU 401 operates the valves v1b to v4b and depressurizes the waste fluid chamber WC1 by the pressure adjustment unit p3 to move the diluted solution in the reaction chambers C1 to C4 to the waste fluid chamber WC1. The first cleaning target flow path is cleaned in such manner.

The CPU 401 then performs a cleaning of the flow path from the reaction chamber C5 to the waste fluid chamber WC2 through the valves v5a, v15, v16, v17 (hereinafter referred to as second cleaning target flow path) (S110). The CPU 401 operates the valves v5a, v15 to v17 to move the diluted cleaning liquid in the reaction chamber C5 to the waste fluid chamber WC2 by the pressure adjustment unit p2 and the diaphragm pump d2. The CPU 401 also operates the valve v5b and depressurizes the pressure adjustment unit p3 to move the diluted solution in the reaction chamber C5 to the waste fluid chamber WC1. The second cleaning target flow path is cleaned in such manner.

Through processes similar to S103 and S104, the CPU 401 causes the piercer 33 to bring the lower end of the piercer 33 into contact with the bottom surface of the cleaning liquid tube W (S111, S112) and causes it to aspirate 1 mL of cleaning liquid (undiluted solution) through the piercer 33 (S113). When the syringe pump S1 is actuated four times, 1 mL of cleaning liquid is aspirated. The piercer 33 then dispenses the aspirated 1 mL of cleaning liquid (undiluted solution) to the reaction chamber C3 (S114).

The CPU 401 then performs a cleaning of the flow path from the reaction chamber C3 to the waste fluid chamber WC2 through the valves v3a, v13, v14 (hereinafter referred to as third cleaning target flow path) (S115). In other words, the CPU 401 operates the valve v3a to move the cleaning liquid (undiluted solution) in the reaction chamber C3 to the waste fluid chamber WC2 by the pressure adjustment unit p1 and the diaphragm pump d1. The CPU 401 also operates the valve v3b and depressurizes the waste fluid chamber WC1 by the pressure adjustment unit p3 to move the cleaning liquid (undiluted solution) in the reaction chamber C3 to the waste fluid chamber WC1. The third cleaning target flow path is cleaned in such manner.

The third cleaning target flow path is again cleaned using the cleaning liquid of undiluted solution because the reaction chamber C3 easily gets dirty by the specimen used for the WNR measurement and because the flow path from the reaction chamber C3 to the waste fluid chamber WC2 through the valves v13, v14 easily gets dirty by the cleaning of the first cleaning target flow path.

Through processes similar to S103 and S104, the CPU 401 causes the piercer 33 to bring the lower end of the piercer 33 into contact with the bottom surface of the cleaning liquid tube W (S116, S117) and aspirate 1 mL of cleaning liquid (undiluted solution) through the process similar to S113 (S118). The piercer 33 then dispenses the aspirated 1 mL of cleaning liquid (undiluted solution) to the reaction chamber C2 (S119).

The CPU 401 operates the valves v11 and v12 to open and operates the pressure adjustment unit p3 to depressurize the waste fluid chamber WC1 to aspirate the cleaning liquid remaining in the cleaning liquid tube W (S120).

Specifically, the CPU 401 performs a timekeeping of an elapsed time from when the aspiration of the cleaning liquid is started, and stops the depressurization of the waste fluid chamber WC1 after elapse of a predetermined time sufficient to aspirate the remaining cleaning liquid. The predetermined time is a minimum required time until the piercer 33 completely aspirates the cleaning liquid and starts to aspirate air, where the predetermined time X is given as B/A (second) where A (mL/sec.) is the aspiration amount per unit time by the pressure adjustment unit p3 and B (mL) is the amount of the residual cleaning liquid in the cleaning liquid tube W.

The air pressure source 307 (see FIG. 6) connected to the pressure adjustment unit p3 is used for the aspiration. The pressure adjustment unit p3 uses the negative pressure generated by the air pressure source 307, so that there is not a limit in the flow volume that can be aspirated through the piercer 33 as opposed to when applying negative pressure to the piercer 33 using the syringe pump S1. Therefore, the cleaning liquid remaining in the cleaning liquid tube W is aspirated all at once through the piercer 33, and moved to the waste fluid chamber WC1.

The CPU 401 then performs a cleaning of the interior of the flow cell of the detector D1 with the cleaning liquid (undiluted solution) (S121). Specifically, the CPU 401 operates the valve v2a to open and operates the pressure adjustment unit p1 and the diaphragm pump d1 to move the cleaning liquid (undiluted solution) in the reaction chamber C2 to the vicinity of the entrance of the detector D1. The CPU 401 then operates the valve v19 and drives the motor M2 to operate the syringe pump S1 to move the cleaning liquid (undiluted solution) near the entrance of the detector D1 into the flow cell of the detector D1 and accumulate therein.

The CPU 401 then performs a cleaning of the discharge line (S122). In the cleaning operation, the diluting solution and the cleaning liquid stored in the waste fluid chambers WC1 and WC2 by the cleaning process up to this step are used. In other words, the CPU 401 operates the valves v20 and v21, adjusts the pressure of the waste fluid chamber WC1 by the pressure adjustment unit p3, and retains the diluting solution and the cleaning liquid in a flow path from the waste fluid chamber WC2 to the valve v21. The discharge line is cleaned in such manner.

After the cleanings in S121 and S122 are performed for a predetermined time, the CPU 401 performs by use of diluting solution a rinsing of the flow path cleaned with the cleaning liquid, that is, the first to third cleaning target flow paths, the interior of the flow cell of the detector D1, and the discharge line (S123). In other words, the CPU 401 operates the fluid circuit to flow the diluting solution from inlet port (not shown) where the diluting solution can be injected to the fluid circuit, operates each mechanism of the fluid circuit, and flows the diluting solution through the first to third cleaning target flow paths, the flow cell of the detector D1 and the discharge line, as shown in the fluid circuit of FIG. 5.

The CPU 401 then causes the liquid in the waste fluid chambers WC1 and WC2 to be discharged (S124). The cleaning process is thereby terminated.

According to the present embodiment, the cleaning liquid in the cleaning liquid tube W is all aspirated in S120 of FIG. 9. Thus, the cleaning liquid in the cleaning liquid tube W does not remain, whereby the cleaning liquid remaining after the aspiration does not spill out from the hole formed in the lid W2 or does not volatilize thus spreading the smell of the cleaning liquid to the surrounding. Even when the cleaning liquid is supplied with a cleaning liquid tube W with the upper part opened, the cleaning liquid remaining after the aspiration is similarly suppressed from spilling or volatilizing. Therefore, according to the present embodiment, the problem caused by the cleaning liquid remaining in the cleaning liquid tube W can be resolved.

Furthermore, according to the present embodiment, when the sample ID is read from the barcode label of the tube by the barcode reader B1a, B2a, a predetermined amount of sample necessary for the measurement is aspirated from the tube (sample tube T). When the cleaning liquid ID is read from the barcode label of the tube by the barcode reader B1a, B2a, the cleaning liquid is aspirated from the tube (cleaning liquid tube W) and the fluid circuit of the measurement unit 3 is cleaned. Thus, the measurement of the sample and the cleaning by the cleaning liquid are switched according to the read content of the barcode reader B1a, B2a, so that the trouble of the user to switch between measurement and cleaning in accordance with the type of tube can be omitted.

According to the present embodiment, the cleaning liquid in the cleaning liquid tube W is first aspirated by the syringe pump S1, and thereafter, the remaining cleaning liquid in the cleaning liquid tube W is aspirated by the pressure adjustment unit p3. Thus, the cleaning liquid aspirated first and the remaining cleaning liquid aspirated later can be used to clean different areas of the fluid circuit, whereby the fluid circuit can be efficiently cleaned.

In the present embodiment, the first to third cleaning target flow paths, the flow cell of the detector D1, and the discharge line are cleaned using the cleaning liquid aspirated first, and one part of the discharge line (flow path from waste fluid chamber WC1 to valve v21) is cleaned using the cleaning liquid aspirated later. The cleaning ranges of the cleaning liquid aspirated first and the cleaning liquid aspirated later may partially overlap or may differ.

Furthermore, according to the present embodiment, the lower end of the piercer 33 is brought into contact with the bottom surface of the cleaning liquid tube W, as shown in FIGS. 4C and 4D. All the cleaning liquid in the cleaning liquid tube W thus can be easily aspirated through the piercer 33.

In the present embodiment, the cleaning liquid in the cleaning liquid tube W can be quantitatively aspirated by the syringe pump S1, and a strong negative pressure can be applied on the piercer 33 by the pressure adjustment unit p3 to aspirate all the cleaning liquid remaining in the cleaning liquid tube W all at once. Thus, the cleaning liquid necessary for cleaning can be quantitatively aspirated, and the cleaning liquid in the cleaning liquid tube W can all be aspirated.

In the present embodiment, when aspirating the sample from the sample tube T, the lower end of the piercer 33 is lowered to a predetermined position above the bottom surface at inside the sample tube T, and the sample is aspirated at such position. Thus, the control of the piercer 33 can be more easily carried out, as opposed to when aspirating the cleaning liquid. When aspirating the sample, the piercer 33 is lowered to pass through the lid T2 of the sample tube T so that the stepping motor 306 does not lose synchronism. Thus, when the piercer 33 is lowered without losing synchronism, the bottom surface of the sample tube T may be damaged when the lower end of the piercer 33 is brought into contact with the bottom surface of the sample tube T. However, in the present embodiment, the bottom surface of the sample tube T is not damaged since the lower end of the piercer 33 is lowered only to the predetermined position above the bottom surface.

The embodiment of the present invention has been described above, but the embodiment of the present invention is not limited thereto.

For instance, the blood is illustrated as the measuring target in the embodiment described above, but the measuring target may be urine. In other words, the present invention can also be applied to a sample analyzer for testing urine, and furthermore, the present invention can be applied to a clinical sample analyzer for testing other clinical samples.

In the embodiment described above, when the cleaning liquid in the cleaning liquid tube W is aspirated by the piercer 33, the pulse N2 is output to the stepping motor 306 to bring the lower end of the piercer 33 into contact with the bottom surface of the cleaning liquid tube W. However, not limited thereto, the lowering position of the piercer 33 may be determined in advance so that the spacing between the lower end of the piercer 33 and the bottom surface of the cleaning liquid tube W becomes small (e.g., within 1 mm). When a strong negative pressure is then applied on the piercer 33 by the pressure adjustment unit p3, the cleaning liquid in the cleaning liquid tube W can all be aspirated. The stepping motor 306 of the embodiment described above is moved by 0.0375 mm per one pulse and can input the pulse in unit of 6 pulses, and hence the position of the lower end of the piercer 33 can be adjusted within 1 mm.

In the embodiment described above, the fluid circuit is cleaned using all the cleaning liquid in the cleaning liquid tube, but not limited thereto, the fluid circuit may be cleaned using one part of the cleaning liquid in the cleaning liquid tube W. In this case, the cleaning liquid not used for cleaning may be discarded, for example.

In the embodiment described above, the waste fluid chamber WC1 is depressurized until a predetermined time X (B/A (sec)) based on the maximum amount of the cleaning liquid contained in the cleaning liquid tube W of B (mL) elapses in the process of S120. However, not limited thereto, the depressurization in the waste fluid chamber WC1 may be carried out based on an amount (B'+Δ) slightly greater than the amount B' (mL) of the cleaning liquid remaining in the cleaning liquid tube W at a stage the process of S120 is carried out. In other words, 4 mL of cleaning liquid is contained in the cleaning liquid tube W at first, and 3.25 mL of cleaning liquid is aspirated by the time of the process of S120 is carried out. Thus, at the stage the process of S120 is carried out, 0.75 mL of cleaning liquid is remaining in the cleaning liquid tube W. Therefore, the depressurization of the waste fluid chamber WC1 may be performed by time (0.75+Δ) minimum required until the piercer 33 completely aspirates 0.75 mL of cleaning liquid and starts to aspirate air.

In the embodiment described above, the waste fluid chamber WC1 is depressurized by a predetermined time to aspirate all the cleaning liquid remaining in the cleaning liquid tube W in the process of S120, but this is not the sole case. For instance, a sensor for detecting the mixing of air may be arranged on the flow path connecting the piercer 33 and the waste fluid chamber WC1, and the waste fluid chamber WC1 may be depressurized from when the aspiration of the cleaning liquid is started until the mixing of the air is detected by the sensor.

In the embodiment described above, the barcode label of the tube is read by the barcode reader B1a, B2a, and whether the type of tube is the sample tube T or the cleaning liquid tube W is determined according to the read content. However, not limited thereto, an RFID (Radio Frequency Identification) may be attached to the tube in place of the barcode label. If the RFID is attached, an antenna for reading the RFID is arranged in place of the barcode reader B1a, B2a.

The shape of the tube may be detected based on the sensor or the imaged image to determine the type of tube instead of determining the type of tube by the barcode reader B1a, B2a. Furthermore, a sensor for irradiating light on the tube and detecting whether the light passes through the tube may be used. In this case, for example, determination is made as the sample tube T containing blood if the light is not transmitted, and determination is made as the cleaning liquid tube W containing the cleaning liquid if the light is transmitted.

In the embodiment described above, the type of tube is determined based on the barcode reader B1a, B2a (S12, S18 of FIG. 8), but not limited thereto, the type of tube may be determined by either barcode reader. In the process of FIG. 8, the necessity of the cleaning process is determined based on the read content by the barcode reader B2a, but the necessity of the cleaning process may be determined based on the read content by the barcode reader B1a or the necessity of the cleaning process may be determined based on the read content by the two barcode readers.

In the embodiment described above, the measurement of the sample and the cleaning by the cleaning liquid are performed according to the type of tube even if the cleaning liquid tube W and the sample tube T are simultaneously held in one sample rack L. However, not limited thereto, only the cleaning liquid tube W may be held in one sample rack L when performing the cleaning by the cleaning liquid. In this case, the rack ID of the sample rack L holding the cleaning liquid tube W may be registered in advance with respect to the information processing unit 4.

In this case, when the rack ID is read from the barcode label L1 of the sample rack L by the barcode reader B1a, the CPU 401 of the information processing unit 4 determines whether or not the rack ID is the sample rack L for holding the cleaning liquid tube W. If the rack ID is the sample rack L for holding the cleaning liquid tube W, the tube held in the sample rack L is transported assuming only the cleaning liquid is contained inside, and the aspiration by the piercer 33 is carried out. In this case, the barcode label W1 attached to the cleaning liquid tube W can be omitted.

In the embodiment described above, the fluid circuit is cleaned using the cleaning liquid aspirated over plural times, but this is not the sole case, and the cleaning liquid in the cleaning liquid tube W may all be aspirated by the piercer 33, and then the aspirated cleaning liquid may be divided to be used for cleaning. In this case, the range of the fluid circuit to clean using a predetermined amount of all the aspirated cleaning liquid and the range of the fluid circuit to clean using the remaining cleaning liquid may be set.

In the process of FIG. 9, the processes of S103 to S107 are repeated for every reaction chamber, but the cleaning liquid for all the reaction chambers may be aspirated by the piercer 33 all at once, an appropriate amount of diluted solution may be mixed into the aspirated cleaning liquid, and thereafter, the diluted cleaning liquid may be dispensed to each reaction chamber from the piercer 33 by a predetermined amount.

In the embodiment described above, when the base 321 is projected out to the front side of the measurement unit 3 and the tube is directly set in the tube setting portion 321a, determination is made on either the sample tube T or the cleaning liquid tube W by the read result of the barcode reader B2a. However, not limited thereto, it may be performed based on the operation procedure and the instruction content of the user.

For instance, determination may be made that the tube is the sample tube T when the tube is directly set in the tube setting portion 321a by the operation of only the open/close button 3a and the start button 3b. Furthermore, determination may be made that the tube is the cleaning liquid tube W when the tube is directly set in the tube setting portion 321a by the operation of only the open/close button 3a and the start button 3b. Moreover, when an instruction of measurement to preferentially perform is input through the information processing unit 4 by the user, and the tube is directly set in the tube setting portion 321a, such tube may be determined as the sample tube T. When a cleaning instruction is input through the information processing unit 4 by the user, and the tube is directly set in the tube setting portion 321a, such tube may be determined as the cleaning liquid tube W.

In the embodiment described above, the measurement order related to each sample is stored in the host computer in advance, but this is not the sole case, and it may be stored in the hard disk 404 of the information processing unit 4. In this case, the processes of S13, S14 of FIG. 8 are omitted, where if the tube positioned at the reading position P3 is the sample tube T (S18: YES), the measurement order stored in the hard disk 404 is read out based on the read content (sample ID) of the barcode reader B2a (S19).

The embodiments of the present invention may be appropriately modified within a scope of the technical concept defined by the Claims.

What is claimed is:

1. A sample analyzer for aspirating and analyzing a sample in a sample tube, the sample analyzer comprising:

an obtaining section that obtains identification information for a tube that identifies a tube type;
a gripping portion that grips the tube;
a fluid processing section that aspirates liquid contained in the tube with a pipette and flows the liquid through a fluid circuit; and
a control unit;
wherein when the control unit identifies the tube type as a sample tube, the control unit controls the gripping portion to grip the sample tube and rotate the sample tube to stir the sample tube, and controls the fluid processing section to aspirate the sample in the sample tube,
when the control unit identifies the tube type as a cleaning liquid tube containing cleaning liquid, the control unit controls the gripping portion to grip the cleaning liquid tube, but does not control the gripping portion to stir the cleaning liquid tube, and then controls the fluid processing section to aspirate substantially all of the cleaning liquid in the cleaning liquid tube with the pipette and to use all or a partial amount of the aspirated cleaning liquid to clean the fluid circuit.

2. The sample analyzer according to claim 1, wherein when the control unit has identified that the tube type is the sample tube, the control unit controls the fluid processing section to aspirate the sample in an amount necessary for a measurement from the sample tube.

3. The sample analyzer according to claim 2, further comprising a detector that detects a component in the sample, wherein when the control unit identifies the tube type as the sample tube, the control unit controls the fluid processing section to flow the aspirated sample toward the detector and obtain a result of detection of the sample by the detector,
when the control unit identifies the tube type as the cleaning liquid tube, the control unit controls the fluid processing section to flow the aspirated cleaning liquid in the fluid circuit.

4. The sample analyzer according to claim 2, wherein when the control unit identifies the tube type as the sample tube, the control unit controls the fluid processing section to aspirate a part of a whole amount of sample in the sample tube,
when the control unit identifies the tube type as the cleaning liquid tube, the control unit controls the fluid processing section to aspirate substantially all of cleaning liquid in the cleaning liquid tube.

5. The sample analyzer according to claim 1, wherein the obtaining section further comprises a barcode reading unit that reads a barcode attached to the tube; and
the control unit identifies the tube type with reference to the identification information obtained by reading the barcode.

6. The sample analyzer according to claim 1, wherein the control unit controls the fluid processing section so as to aspirate a predetermined amount of cleaning liquid from the cleaning liquid tube with the pipette, and then to aspirate a remaining cleaning liquid contained in the cleaning liquid tube with the pipette.

7. The sample analyzer according to claim 6, wherein the control unit controls the fluid processing section to use a first flow path for flowing the predetermined amount of cleaning liquid aspirated with the pipette and to use a second flow path for flowing the remaining cleaning liquid aspirated with the pipette.

8. The sample analyzer according to claim 1, wherein the control unit controls the fluid processing section to aspirate the cleaning liquid by applying negative pressure in the pipette when aspirating the cleaning liquid from the cleaning liquid tube.

9. The sample analyzer according to claim 8, wherein the control unit controls, when aspirating the cleaning liquid from the cleaning liquid tube, the fluid processing section to bring a distal end of the pipette into contact with an inner bottom of the cleaning liquid tube and to aspirate the cleaning liquid.

10. The sample analyzer according to claim 1, wherein the fluid processing section includes a quantitative syringe pump that applies a negative pressure in the pipette to aspirate a constant amount of liquid, and an air pressure source; and
the control unit controls the fluid processing section to aspirate a constant amount of cleaning liquid from the cleaning liquid tube using the quantitative syringe pump and to aspirate the remaining cleaning liquid from the cleaning liquid tube using the air pressure source.

11. The sample analyzer according to claim 10, wherein the control unit further controls the gripping portion to stir the sample tube and wherein the stirring of the sample tube includes tilting the sample tube until a bottom of the sample tube is at a position higher than a head of the sample tube.

12. A sample analyzer for aspirating and analyzing a sample in a sample tube, the sample analyzer comprising:
an obtaining section that obtains identification information for a tube that identifies a tube type;
a gripping portion for gripping the tube;
a fluid processing section that aspirates liquid contained in the tube with a pipette and flows the liquid through a fluid circuit; and
a control unit;
wherein when the control unit identifies the tube type as a sample tube, the control unit controls the gripping portion to grip the sample tube and rotate the sample tube to stir the sample tube, and controls the fluid processing section to aspirate the sample in the sample tube,
when the control unit identifies the tube type as a cleaning liquid tube containing cleaning liquid, the control unit controls the gripping portion to grip the cleaning liquid tube, but does not control the gripping portion to stir the cleaning liquid tube, and controls the fluid processing section to aspirate a predetermined amount of cleaning liquid for cleaning the fluid circuit from the cleaning liquid tube and then to aspirate remaining cleaning liquid in the cleaning liquid tube.

13. The sample analyzer according to claim 12, wherein the same pipette aspirates the predetermined amount of cleaning liquid and aspirates the remaining cleaning liquid.

14. The sample analyzer according to claim 13, wherein the control unit controls the fluid processing section to flow the remaining cleaning liquid through a flow path that is different from a flow path of the cleaning liquid.

15. The sample analyzer according to claim 12, wherein the control unit controls, when aspirating the cleaning liquid from the cleaning liquid tube, the fluid processing section to bring a distal end of the pipette into contact with an inner bottom of the cleaning liquid tube and to aspirate the cleaning liquid.

16. A sample analyzer for aspirating and analyzing a sample in a sample tube, the sample analyzer comprising:
an obtaining section that obtains identification information that identifies a tube type;
a gripping portion for gripping the sample tube;

a fluid processing section that aspirates liquid contained in the sample tube with a pipette and flows the liquid through a fluid circuit; and a control unit;

wherein when the control unit identifies the tube type as the sample tube, the control unit controls the gripping portion to grip the sample tube and rotate the sample tube to stir the sample tube, and controls the fluid processing section to aspirate the sample in the sample tube, when the control unit identifies the tube type as a cleaning liquid tube containing cleaning liquid, the control unit controls the gripping portion to grip the cleaning liquid tube, but does not control the gripping portion to stir the cleaning liquid tube, and the control unit controls the fluid processing section to bring the pipette into contact with an inner bottom of the cleaning liquid tube and to aspirate the cleaning liquid while the pipette contacts the inner bottom, thus cleaning the fluid circuit using all or a partial amount of the aspirated cleaning liquid, and wherein the control unit controls the fluid processing section to continue to apply a negative pressure in the pipette while maintaining the pipette in contact with the inner bottom of the cleaning tube until aspiration of air by the pipette is started.

17. The sample analyzer according to claim 16, wherein when the control unit has identified by the identification section that the tube is the sample tube containing the sample, the control unit controls the fluid processing section to lower the pipette to a predetermined height that is inside the sample tube and above the inner bottom, and aspirate the sample at the predetermined position.

18. The sample analyzer according to claim 16, wherein the obtaining section further comprises a barcode reading unit that reads a barcode attached to the tube; and the control unit identifies the tube type from the identification information.

19. A sample analyzer for aspirating and analyzing a sample in a sample tube, the sample analyzer comprising:

an obtaining section that obtains identification information that identifies a tube type;

a gripping portion for gripping the sample tube;

a fluid processing section that aspirates a liquid contained in the sample tube with a pipette and flows the liquid through a fluid circuit; and a control unit;

wherein when the control unit identifies the tube type as the sample tube, the control unit controls the gripping portion to grip the sample tube and rotate the sample tube to stir the sample tube, and controls the fluid processing section to aspirate the sample in the sample tube, when the control unit identifies the tube type as a cleaning liquid tube containing cleaning liquid, the control unit controls the gripping portion to grip the cleaning liquid tube, but does not control the gripping portion to stir the cleaning liquid tube, and controls the fluid processing section to aspirate substantially all of a cleaning liquid in a cleaning liquid tube with the pipette and to use all of the aspirated cleaning liquid to clean the fluid circuit, wherein the fluid processing section includes a quantitative syringe pump that applies a negative pressure in the pipette for aspirating a constant amount of liquid in the pipette, and an air pressure source; and the control unit controls the fluid processing section to aspirate a constant amount of cleaning liquid from the cleaning liquid tube using the quantitative syringe pump and to aspirate the remaining cleaning liquid from the cleaning liquid tube using the air pressure source.

20. A sample analyzer for aspirating and analyzing a sample in a sample tube, the sample analyzer comprising:

an obtaining section that obtains identification information for a tube that identifies a tube type;

a gripping portion that grips the tube;

a fluid processing section that aspirates liquid contained in the tube with a pipette and flows the liquid through a fluid circuit; and a control unit;

wherein when the control unit identifies the tube type as the sample tube, the control unit controls the gripping portion to grip the sample tube and rotate the sample tube to stir the sample tube, and controls the fluid processing section to aspirate the sample in the sample tube, when the control unit identifies the tube type as a cleaning liquid tube containing cleaning liquid, the control unit controls the gripping portion to grip the cleaning liquid tube, but does not control the gripping portion to stir the cleaning liquid tube and then controls the fluid processing section to bring the pipette into contact with an inner bottom of the cleaning liquid tube and to aspirate the cleaning liquid while the pipette contacts the inner bottom, thus cleaning the fluid circuit using all or a partial amount of the aspirated cleaning liquid.

* * * * *